United States Patent [19]
Griffin et al.

[11] Patent Number: 5,429,119
[45] Date of Patent: Jul. 4, 1995

[54] HAND-HELD COMPACT DIAGNOSTIC DEVICE

[75] Inventors: J. Michael Griffin, Syracuse; William R. Witkowski, Marcellus, both of N.Y.

[73] Assignee: Welch Allyn, Inc., Skaneateles Falls, N.Y.

[21] Appl. No.: 117,405

[22] Filed: Sep. 3, 1993

[51] Int. Cl.⁶ .......................................... A61B 1/227
[52] U.S. Cl. ........................... 600/200; 362/109; 362/804; 403/59; 403/93; 403/103
[58] Field of Search .................. 128/9, 23; 362/109, 362/119, 120, 198, 804, 197, 277; 403/59, 58, 53, 93, 96, 103; 446/97, 383, 384, 487; 132/294, 308, 286

[56] References Cited

U.S. PATENT DOCUMENTS

| | | | |
|---|---|---|---|
| 1,682,444 | 8/1928 | Trumpler | 403/59 X |
| 1,900,906 | 3/1933 | Brown | 362/117 |
| 3,812,847 | 5/1974 | Moore et al. | |
| 4,190,982 | 3/1980 | Rahmstorf | 446/384 |
| 4,208,703 | 6/1980 | Orr | 362/109 X |
| 4,878,156 | 10/1989 | Hallings et al. | 362/804 X |
| 4,968,282 | 11/1990 | Robson et al. | 446/383 X |
| 4,991,069 | 2/1991 | Tiller | |
| 5,062,179 | 11/1991 | Huang | 403/93 X |
| 5,278,739 | 1/1994 | Gammache | 362/197 |

Primary Examiner—Richard J. Apley
Assistant Examiner—Donna L. Maraglio
Attorney, Agent, or Firm—Harris Beach & Wilcox

[57] ABSTRACT

A hand-held compact diagnostic device is provided with a pair of instrument heads each requiring an independent source of illumination. The instrument heads may be rotated into a fully extended position and once therein, may be smoothly turned through 360 degrees in consecutive ninety degree intervals to accommodate any preferred orientation desired by the user. Each instrument head is biased in the fully extended position and a rotated closed position. Each instrument head is also adjustably biased to an aligned position for proper closure by the interaction of an adjustment collar with a pair of ball detents. The adjustment collar further biases each head in three additional positions at ninety degree intervals for use when fully extended. A pair of central terminals maintain continuous contact between each rotatable head of the device while a pair of radial terminals are in electrical contact only when the instrument head is in a fully extended position. When the instrument head is rotated into the closed position, the radial terminals disengage to open the circuit between the source of illumination in the instrument head and a battery source contained within the device.

17 Claims, 4 Drawing Sheets

HAND-HELD COMPACT DIAGNOSTIC DEVICE

BACKGROUND OF THE INVENTION

1. Field of the Invention

This invention relates in general to portable or hand-held medical diagnostic devices and, in particular, to a compact device having an adjustable adaptor for accommodating a variety of different heads. More specifically, but without restriction to the particular embodiment hereinafter shown and described, this invention relates to a compact device having a pair of instrument heads which are independently extendable and, once extended, smoothly turnable through 360 degrees in consecutive ninety degree increments.

2. Discussion of the Prior Art

The art of hand-held compact diagnostic devices has been contributed to by a number of proposed devices including, for example, the handle-case disclosed in U.S. Pat. No. 3,812,847 which issued to W. C. Moore et al. May 28, 1974. These devices are conveniently carried by doctors and practitioners periodically or throughout the entire work day, thus making them readily available when needed.

The Moore et al. device includes a pair of illuminated medical instrument heads which are each permanently secured to a corresponding base contained in the handle-case. When the case is opened, the base allows the instrument head to be folded out with a predetermined orientation. Once the instrument is folded out, it is positionable in any one of six possible orientations relative to the handle-case. The six orientations include the predetermined orientation which is required to fold the instrument into the case and properly close the cover thereover.

In other prior devices wherein the instrument head is releasable from the base, the predetermined orientation aligned for proper closure requires precise and costly machining to time the threads on the base to those provided in the neck of the instrument head so that when the instrument is tightly screwed to the base, the head obtains the desired predetermined orientation. It is only with this predetermined orientation that the cover may be properly closed against the case. Since the typical instrument head has an irregular shape, folding the instrument into the case with any other orientation would result in a portion of the instrument projecting out of the case thus interfering with the cover and preventing proper closure. The precise machining required to give the instrument head the desired orientation serves as an impediment to providing the device with optional instrument heads. This is true because of manufacturing difficulties encountered in providing a new instrument head having a different irregular shape with the exact timing of threads needed to give the instrument the desired predetermined orientation required for proper closing of the case cover.

Previously proposed compact diagnostic devices are thus limited in that they are either unable to accommodate any type of interchangeable head since the head is permanently attached to the base, as in the Moore et al. device discussed above, or require expensive and precise machining which hinders the option of providing a variety of different compatible heads. Such devices are further limited in restricting the number of possible orientations once the head is extended.

OBJECTS AND SUMMARY OF THE INVENTION

It is, therefore, an object of the present invention to improve hand-held compact diagnostic devices.

It is still a further object of the present invention to enable each head of a pair of instrument heads of a hand-held compact diagnostic device to smoothly swivel when a respective head is in a fully extended position.

A further object of the present invention is to bias each instrument head of a compact diagnostic device in a contained closed position and in a fully extended position.

Still another object of the present invention is to bias each instrument head of a compact diagnostic device in an aligned position for proper closing in a containment area of the device.

An additional object of the present invention is to bias each instrument head of a compact diagnostic device, when in a fully extended usable position, in a number of different potentially preferred directional orientations.

It is still a further object of the present invention to utilize an adjustment collar for each head in a hand-held compact diagnostic device so that a variety of different instrument heads can be easily biased in an aligned position for proper closure within the device.

Yet another object of the present invention is to accommodate a variety of interchangeable instrument heads in a hand-held compact diagnostic device by utilizing a universal instrument adaptor.

Still an additional object of the present invention is to enable each instrument head of a pair of instrument heads contained in a hand-held compact diagnostic device to receive electric current to power a source of illumination contained within the head when the head is in a fully extended position.

It is still yet a further object of the present invention to electrically disconnect each instrument head of a pair of instrument heads contained in a hand-held compact diagnostic device from a battery source contained in the device when the head is moved from a fully extended position to a closed position within the device.

These and other objects are attained in accordance with the present invention wherein there is provided a hand-held compact diagnostic device for a pair of instruments. Each of the instruments has an operative head for diagnostic purposes which is connected to a neck portion. The neck of the instrument is secured to a swivel adaptor provided in the device which is adapted to receive a source of illumination. The instrument heads of the device may be selected from a wide range of different possible medical and non-medical instruments requiring a source of illumination.

In accordance with one aspect of the present invention, the compact device includes an elongated case with an opening provided at each end. The elongated case has an axis of elongation and is provided with a hinged cover that extends from one of the open ends to the other. This cover encloses a corresponding containment area within the case into which the instrument heads are closed when not in use. A pivot or rotation housing is provided within each open end of the elongated case. The rotation housing enables a respective instrument head to rotate through approximately 180 degrees about its axis of rotation from a closed position within the containment area to a fully extended position. The swivel adaptor has a central axis and is secured within the rotation housing. In the preferred embodiment of the present device, the swivel adaptor includes a single helical thread that quickly and securely mates with a corresponding thread provided in the neck of a respective instrument head. The swivel adaptor enables the respective instrument head to be smoothly turned through 360 degrees around the central axis when the instrument head is in the fully extended position.

According to another aspect of the present invention, the compact diagnostic device is provided with an adjustment collar around the swivel adaptor which is secured thereagainst when the respective instrument head is aligned in a position relative to the containment area so that the head may be rotated into the elongated case and the cover properly closed over the head. A spring urged ball detent is provided in the rotation housing and interacts with a series of apertures in the collar to bias the swivel adaptor in the position aligned for closing as well as in other potentially preferred directions for use by the practitioner. The adjustment collar of the present invention in combination with the ball detent thus allows the respective instrument head, and other interchangeable heads, to be quickly aligned and biased for proper closing as well as biased in other potentially preferred orientations for use in the fully extended position.

In accordance with yet another aspect of the present invention, each end of the preferred embodiment of the elongated case is provided with a pair of raised annular bosses to secure the rotation housing therebetween. One of the pair of bosses is provided with a central and a radial electrical terminal. Each of these terminals is connected to a battery source provided in the device. In cooperative association therewith, one side of each of the rotation housings is provided with a pair of corresponding terminals in electrical contact with the swivel adaptor in such a manner so as to allow the adaptor to be turned through 360 degrees without losing contact with the rotation housing terminals. The corresponding central terminals are in continuous contact, while the radial terminals are positioned so that they are only in contact when the respective instrument head is fully extended to a usable position. When the head is rotated into the closed position, the radial terminal on the rotation housing moves off the corresponding radial terminal provided within the raised annular boss along a predetermined arc of rotation. Thus, when the respective head is in the closed position, the source of illumination is disconnected from the battery.

BRIEF DESCRIPTION OF THE DRAWING

Further objects of the present invention together with additional features contributing thereto and advantages accruing therefrom will be apparent from the following description of a preferred embodiment of the invention which is shown in the accompanying drawing with like reference numerals indicating like components throughout, wherein.

DETAILED DESCRIPTION OF A PREFERRED EMBODIMENT

Figure 1:
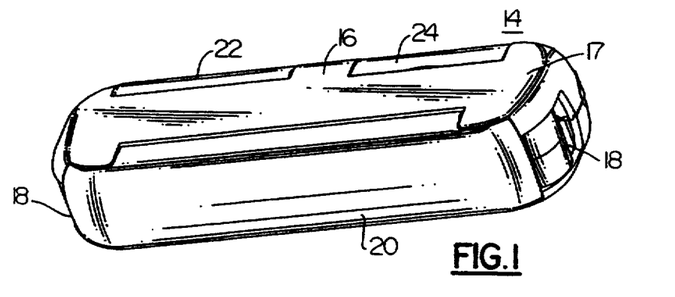
FIG. 1 is a perspective view of the hand-held compact diagnostic device of the present invention in the fully closed condition.
Figure 2:
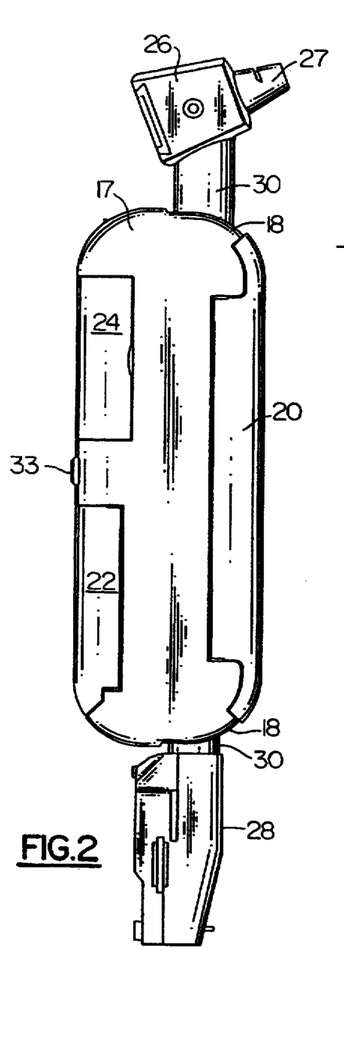
FIG. 2 is a side elevational view of the device of FIG. 1 showing both instrument heads in their fully extended positions.
Figure 3:
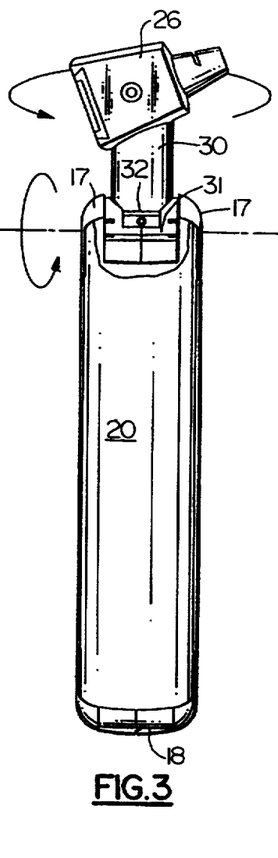
FIG. 3 is a front elevational view of the present compact diagnostic device showing one of the instrument heads in the fully extended position and the other in the closed and covered position.

Referring now to the drawing and initially to FIGS. 1-3, there is shown a hand-held compact diagnostic device 14 in accordance with the present invention. This type of device is commercially available through Welch Allyn, Inc. of Skaneateles Falls, N.Y. The illustrated device includes an elongated case 16 having a generally rectangular cross-section taken perpendicular to its axis of elongation. The elongated case 16 includes a pair of opposed parallel side walls 17 which terminate at open ends 18. An elongated cover 20 extends from one of the open ends 18 to the other open end 18. The elongated case 16 also includes smaller covers 22 and 24. The preferred embodiment of the hand-held compact diagnostic device 14 includes a pair of instrument heads 26 and 28. In the device illustrated in FIGS. 1-3, instrument head 26 is an otoscope including a speculum portion 27 and instrument head 28 is an ophthalmoscope. The device of the present invention, however, is not limited to these particular instrument heads, and is adapted to accommodate any one of a number of possible medical or non-medical instrument heads requiring a source of illumination.

Each of the instrument heads 26 and 28 includes a neck portion 30 which is connected to a pivot or rotation housing 31 that is generally cylindrical in shape. The rotation housing 31 includes a swivel adaptor 32 which is utilized to secure the neck 30 of a respective instrument head to the compact device 14. The elongated case 16 also includes a three-way switch 33 which has three positions including a central off position, a left position for low intensity light, and a right position for high intensity light. With reference to FIG. 3, it is shown that the swivel adaptor 32 has a central axis about which a respective instrument head may be smoothly turned through 360 degrees while the rotation housing 31 has a rotation axis which allows the head to be rotated through approximately 180 degrees from a fully extended position shown by instrument head 26 in FIG. 3 to a fully closed and covered position as represented by instrument head 28 in FIG. 3. The housing 31 and adaptor 32 will be described in further detail hereinafter.

Figure 4:
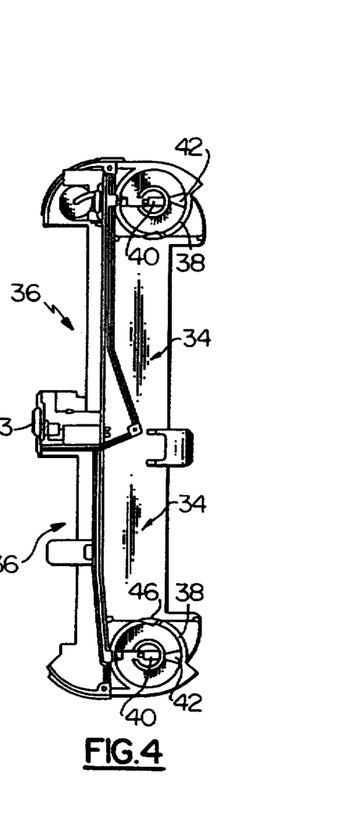
FIG. 4 is a cross sectional view of the elongated case of the device of the present invention.
Figure 10:
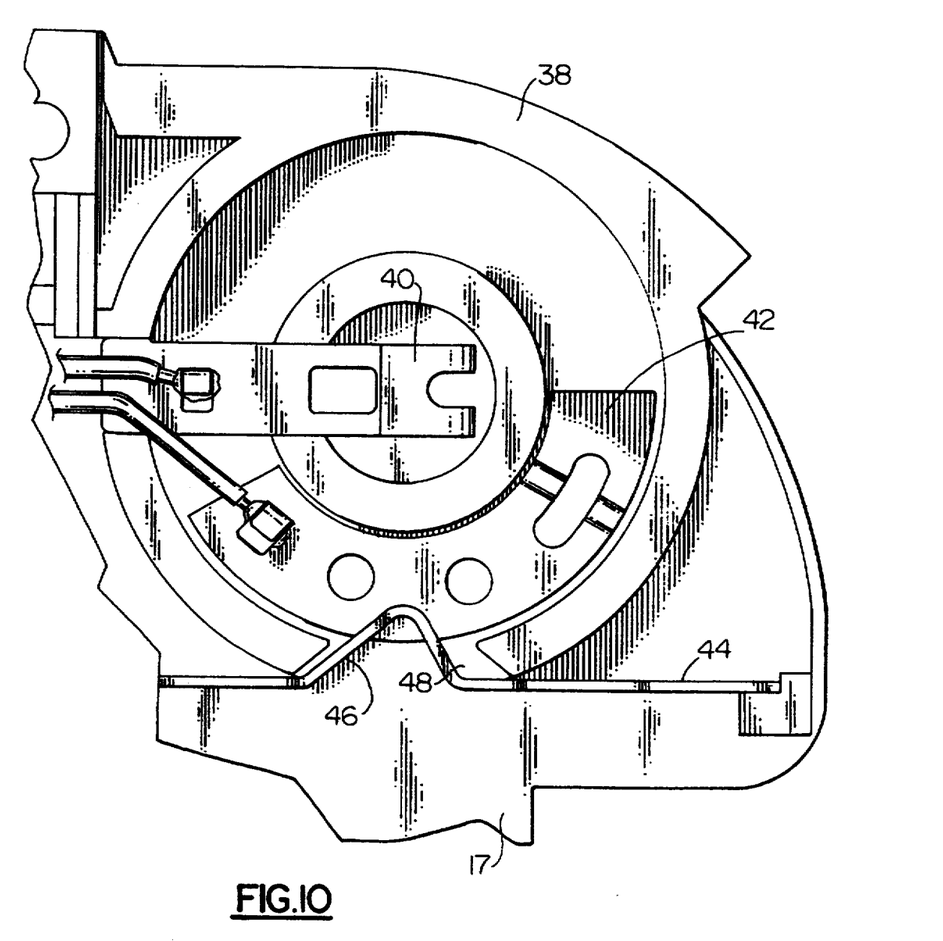
FIG. 10 is an enlarged plan view of one of the end regions of the elongated case as shown in FIG. 4.

With reference now to FIGS. 4 and 10, it is shown that the elongated case 16 includes a containment area 34 into which the instrument heads 26 and 28 may be rotated when not in use. The elongated case 16 also includes a pair of auxiliary compartments 36. One of the auxiliary compartments 36 is used to contain a rechargeable battery pack, a pair of primary cells, or any suitable battery source (not shown). The other auxiliary compartment 36 in the device illustrated in the drawing is used to contain a clip of replacement speculum tips (not shown) in a manner known in the art.

Each of the end portions of the opposing parallel side walls 17 include a raised annular boss 38 as represented in FIGS. 4 and 10. Thus, for each open end 18 of the elongated case 16, a pair of opposing raised annular bosses 38 is provided. One of each of the pair of raised annular bosses 38 includes a central electrical terminal 40 as well as a radial electrical terminal 42. The central electrical terminal 40 is positioned in the geometrical center of the raised annular boss 38 while the radial electrical terminal 42 is positioned on a radius extending out from the center of the annular boss 38 which is positioned 90 degrees relative to the axis of elongation of the case. As shown most clearly in FIG. 10, each raised annular boss 38 includes a flat spring 44 extending through a point tangential to the raised annular boss 38. The flat spring 44 includes a pawl 46 which protrudes into the interior of the raised annular boss 38 through an opening 48 provided at the tangent point.

Figures 5, 6, 6A:
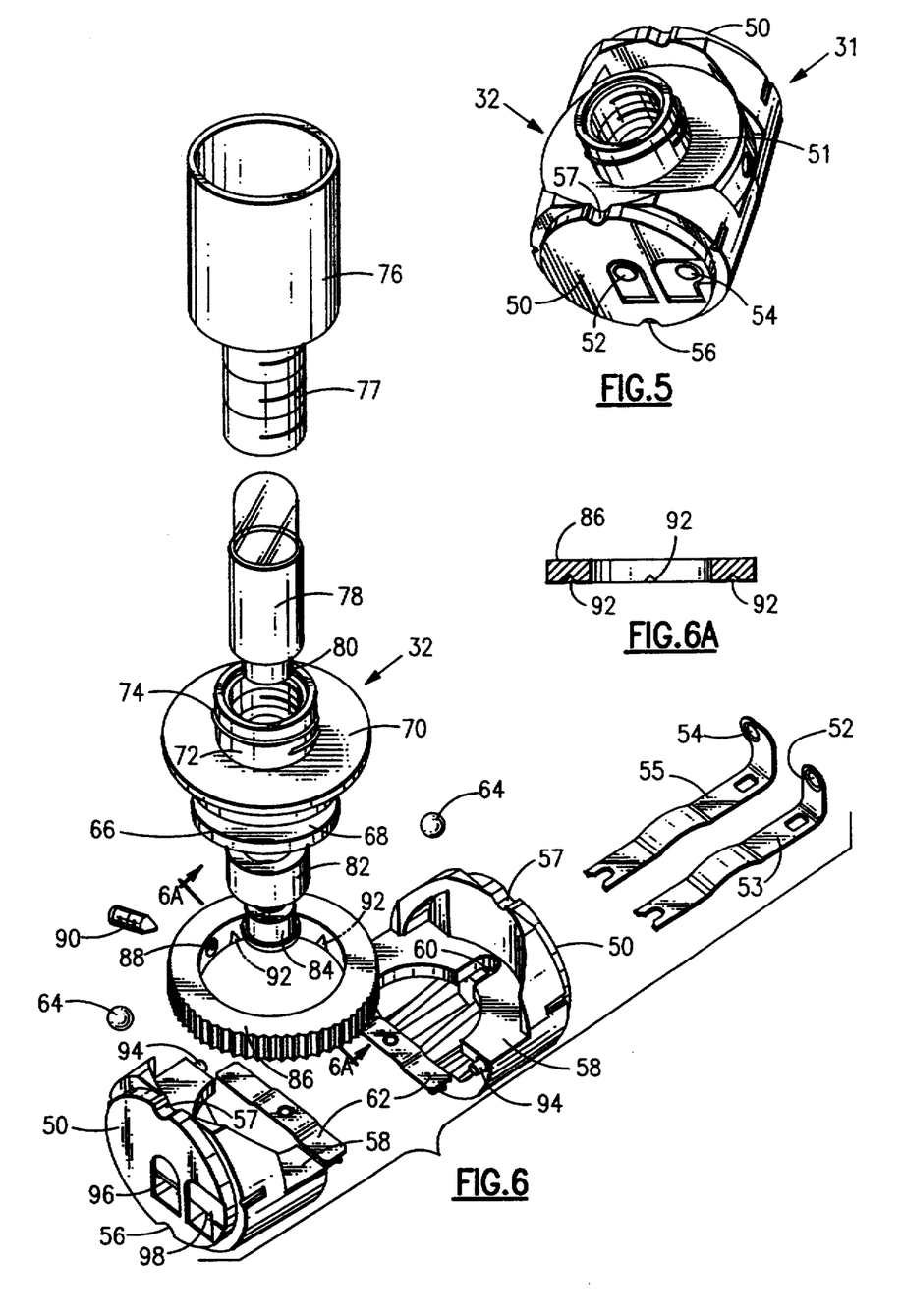
FIG. 5 is an isolated perspective view of the assembled rotation housing and swivel adaptor.
FIG. 6 is an exploded perspective view of the housing and adaptor of FIG. 5 showing a lamp assembly for an instrument head and an adjustment collar in accordance with the present invention.
FIG. 6A is a cross sectional view of the adjustment collar taken along section line 6A—6A of FIG. 6.
Figure 7:
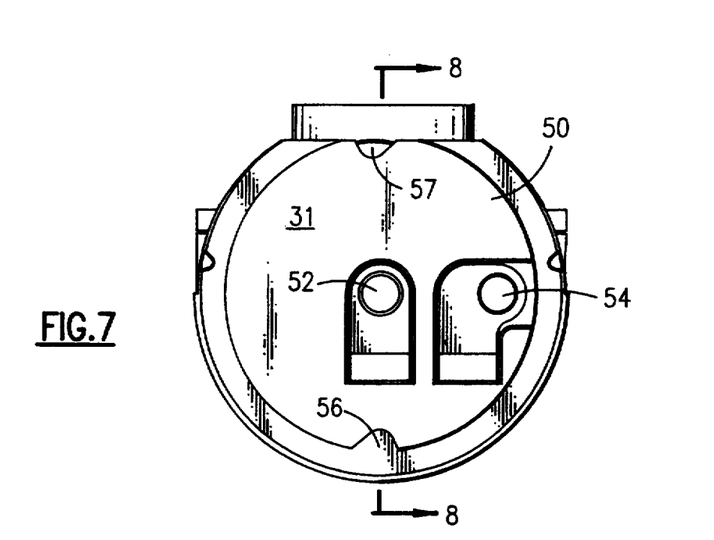
FIG. 7 is an elevational end view of the rotation housing including a pair of electrical terminals.

Referring now to FIGS. 5 and 6, it is shown that the generally cylindrically shaped rotation housing 31 includes a pair of opposed circular end faces 50 formed in the side of the rotation housing 31 and a circular opening 51 extending between the end faces 50. One of the two end faces 50 includes a central electrical terminal 52 which is formed on a central connector 53 and a radial terminal 54 which is similarly made a part of a radial connector 55. Each of the end faces 50 includes a pair of diametrically opposed notches 56 and 57 that are placed along a diameter parallel to the axis of elongation when the respective instrument head is in either the fully extended or closed position. When the rotation housing 31 is assembled between the opposing parallel side walls 17 and secured within a pair of corresponding raised annular bosses 38, the instrument head will be biased in both the fully extended position as well as the fully closed position. This biasing action is achieved by the flat spring 44 and pawl 46 as best shown in FIG. 10. When the instrument head is rotated into the fully extended position, the pawl 46 will snap into notch 56 thereby biasing the instrument head in the open position. When the instrument head is rotated through 180 degrees to its closed position, the pawl 46 will similarly snap into the other notch 57. Thus in this manner, a practitioner using the instrument will be reassured when the instrument is both properly extended and properly closed.

Figure 8:
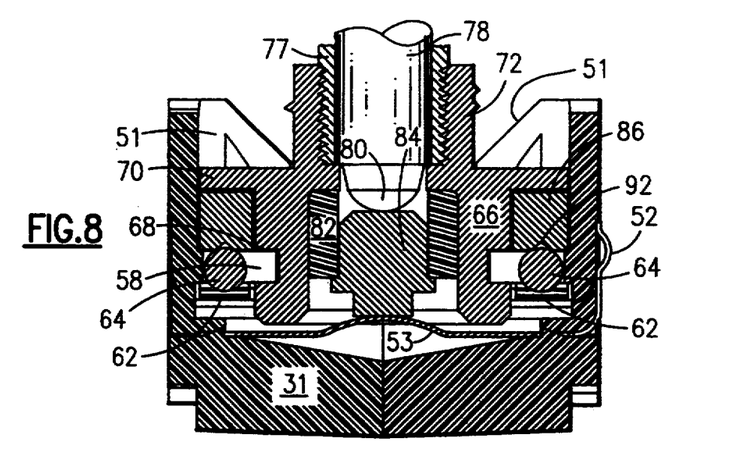
FIG. 8 is a cross sectional view of the housing of FIG. 7 taken along section line 8—8 and including the swivel adaptor.

In FIGS. 6 and 8, it is shown that the rotation housing 31 includes an inwardly directed annular rim 58. Each half of the rim 58 is provided with a slot 60 as shown in FIG. 6. Positioned below each of the slots 60 is spring 62 that retains a ball detent 64. The ball detent 64 is positioned substantially below the annular rim 58 in such a manner that when the spring 62 is in an unstressed condition, a portion of the ball detent will slightly protrude above the annular rim 58. Referring now to the swivel adaptor 32, it is shown in FIGS. 6 and 8 that the adaptor includes a generally cylindrical base member 66 which has an annular groove 68 formed thereabout, an outwardly directed circular flange 70, and an upwardly directed hollow shaft segment 72. The shaft segment 72 includes a single helical thread on an outer circumference which is designed to quickly mate with a corresponding thread formed on an inside circumference of the neck 30 of a respective instrument head. The single helical thread 74 is intended to provide quick assembly and disassembly of a respective instrument head to the hand-held compact device 14.

The swivel adaptor 32 is adapted to receive a lamp housing 76 having a threaded mounting segment 77 which threads into the interior of the hollow shaft 72. This arrangement for the lamp housing is used in conjunction with the otoscope as illustrated by the instrument head 26, and may also be used by other instrument heads having a similar lamp housing arrangement. The lamp housing 76 receives a lamp 78 in a sliding fit within the interior of the threaded segment 77. The lamp 78, as used in any instrument head in accordance with the present invention, includes an insulated electric terminal 80. Upon assembly, the lamp 78 is inserted into the interior of the segment 77 and the lamp housing 76 is then securely threaded into the swivel adaptor 32 thus completing a subassembly. In the ophthalmoscope comprising the instrument head 28, the lamp housing 76 is secured within the instrument head and does not require threads on the segment into which the lamp 78 is slideably received. For this type of instrument head, the internal threads in the shaft segment 72 are not required. The swivel adaptor 32 is further provided with an insulator ring 82 which is positioned in the interior of the cylindrical base member 66. A terminal plug 84 inserts into the interior of the insulator ring 82 to contact the terminal 80 of lamp 78.

The rotation housing 31 and swivel adaptor 32 assembly further include an adjustment collar 86 which is provided with a threaded horizontal aperture 88 and a set screw 90 threadably receivable therein. A series of four conical, bottom countersinks or apertures 92 is positioned on the bottom face of the adjustment collar 86. The apertures 92 are spaced ninety degrees relative one another as shown in FIGS. 6 and 6A. For conveniently and clearly describing the present invention, the various directional references used herein are taken relative to the reference frame of the drawing, it being understood that in actual use of the present device, relative directional references may be inverted, reversed, or otherwise reorientated. The horizontal aperture 88 is offset by approximately eighteen degrees from one of the conical apertures 92 as shown in FIG. 6. The rotation housing 31 is comprised of two identical half sections. This results in a manufacturing advantage since only one forming process is required to fabricate both halves. The two halves of the rotation housing 31 are secured together by use of assembly pins 94 in an ultrasonic assembly technique known in the art.

Prior to assembling the two halves of the rotation housing 31, the adjustment collar 86 including the set screw 90 is positioned between the lower portion of the outwardly directed circular flange 70 which will place the bottom face of the collar 86 flush with the upper edge of the annular groove 68 as shown in FIG. 8. After each of the detent assemblies including the balls 64 and the springs 62 is completed, each half of the rotation assembly is positioned relative to the swivel adaptor 32 with the inwardly directed annular rim 58 being inserted into the corresponding annular groove 68. The housing halves then undergo ultrasonic assembly to complete the unitary subassembly including the rotation housing and the swivel adaptor. The connectors 53 and 55 are then inserted through the side of one of the circular end faces 50, respectively through apertures 96 and 98 formed therein. As shown in FIG. 8, the central connector 53 will contact the terminal plug 84, which in turn is in contact with the insulated electrical terminal 80 of the lamp 78 inside the lamp housing 76. After insertion, the radial connector 55 will contact the lower edge of the cylindrical base member 66. To make a functioning circuit between the terminals 52 and 54 and the lamp 78, the material forming the rotation housing 31 is selected from a number of suitable non-conducting materials while the swivel adaptor 32 is formed from an electrically conducting material. In this manner, the swivel adaptor 32 may be continuously turned through 360 degrees about its central axis while the central connector 53 maintains electrical contact with the terminal plug 84 and the radial connector 55 maintains electrical contact with the cylindrical base member 66.

Upon final assembly, when the rotation housing 31 and swivel adaptor 32 subassembly is secured between a pair raised annular bosses 38 on the opposing parallel side walls 17 in a respective open end 18, the central terminal 52 will be in continuous contact with the central terminal 40 provided within the raised annular boss 38. The radial terminal 54 of the housing 31 will be in electrical contact with the corresponding radial terminal 42 of the annular boss 38 only when the instrument head is in the fully extended position. When the respective instrument head is rotated into the closed position, the radial terminal 54 of the circular end face 50 will rotate off the corresponding radial terminal 42 along a predetermined arc of rotation so that the electrical circuit between the battery source and the lamp is opened. In this position, the three-way switch 33 becomes inoperative with respect to the closed instrument head.

Figure 9:
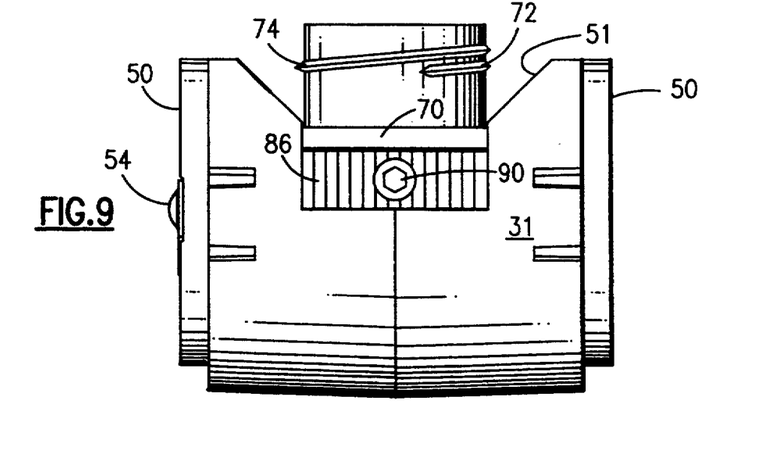
FIG. 9 is a side elevational view of the housing and adaptor assembly shown in FIG. 5.

In accordance with one aspect of the present invention, it is desired to provide the elongated case 16 with the smallest possible dimensions while still accommodating a variety of possible interchangeable instrument heads. This variety of instrument heads includes various irregular shapes as represented by the shapes of the instrument heads 26 and 28. It is thus apparent that a selected instrument head will require a particular orientation to be completely closed within the containment area 34 without obstructing proper closure of the elongated cover 20 thereover. As discussed above, a selected instrument head can be readily secured to the swivel adaptor 32 by means of the single helical thread 74. The head is thus free to turn through 360 degrees about the central axis of rotation. At this point the set screw 90 has not been secured against the cylindrical base member 66 of the swivel adaptor 32. To give the selected instrument head the proper orientation with respect to the containment area, the head is rotated into the closed position and adjusted within the containment area 34 so that the elongated cover 20 may be properly closed thereover. The adjustment collar 86 is then turned until the ball detents 64 protrude into the pair of diametrically opposed conical apertures 92 which does not include the threaded horizontal aperture 88 adjacent thereto. When the ball detents 64 are thus positioned within the conical apertures 92, a clicking sound may be heard and the collar 86 will experience a slight resistance to further turning. This will position the set screw 90 in an access area within the rotation housing 31 as shown in FIG. 9. When the proper alignment is determined so that the instrument head may be completely enclosed in the containment area 34, the set screw is tightened against the cylindrical base member 66. In this manner, one of the detent positions of the swivel adaptor has been adjusted or set for the specific instrument head such that it will be biased in a position aligned for proper closure within the containment area 34. In accordance with the number and placement of the conical apertures 92 in the preferred embodiment, the instrument head will be biased in any one of four potentially preferred detent positions including the position aligned and biased for proper closure. Thus, the instrument head is smoothly turnable through 360 degrees in consecutive ninety degree increments or intervals and is easily swiveled into any one of the four biased detent positions or anywhere between consecutive detent positions. The present invention, however, is not limited to any specific number of detent positions but does include at least one detent position to bias the instrument head in a position aligned for proper closure.

When the instrument head has been placed in the fully extended position and turned to any biased or unbiased preferred directional orientation for use, it may be easily returned to the previously set detent position aligned and biased for proper closure. This aligned position will be readily apparent to the user through familiarity with the particular instrument head. In this detent position, the practitioner is assured that the head is in proper alignment for rotating the head into the containment area so that the elongated cover is completely closeable thereover.

While this invention has been described in detail with reference to a certain preferred embodiment, it should be appreciated that the present invention is not limited to that precise embodiment. Rather, in view of the present disclosure, many modifications and variations would present themselves to those of skill in the art without departing from the scope and spirit of this invention, as defined in the following claims.

What is claimed is:

1. A hand-held compact diagnostic device comprising:
at least one instrument head having a source of illumination and a proximal end;
a case including first openable cover means for enclosing a corresponding containment area for said at least one instrument head;
rotation means positioned within said case for rotating a respective instrument head about an axis of rotation from a closed position within the containment area to a fully extended position; and
swivel means having a central axis, being cooperatively engaged with said rotation means, and adapted to securely receive said respective instrument head, said swivel means including means for enabling said respective instrument head to be smoothly turned through consecutive degrees of rotation around said central axis and along a predetermined arc length when the instrument head is in the fully extended position so that said respective instrument head is positionable at any point along said predetermined arc length, said swivel means further including detent means for biasing said fully extended instrument head into at least one potentially preferred position along said predetermined arc length,
whereby said at least one instrument head is movable from a contained closed position within said case, to a plurality of fully extended positions suitable for inspection or diagnostic purposes.

2. The hand-held compact diagnostic device according to claim 1 further including adjustment means for setting said respective instrument head in an aligned position relative to the containment area so that the head may be closed therein with said first cover means completely shut thereover and wherein said detent means biases said swivel means so that said aligned position corresponds to said at least one preferred position.

3. The hand-held compact diagnostic device according to claim 2 wherein said case is an elongated case having an axis of elongation and at least one opening at an end thereof, said first cover means is parallel to said axis of elongation and extends from said at least one opening along a predetermined length of the case, and said axis of rotation is perpendicular to said axis of elongation.

4. The hand-held compact diagnostic device according to claim 3 wherein said elongated case has a generally rectangular cross section taken on a plane perpendicular to said axis of elongation, said at least one opening thereby being formed by a pair of opposed parallel side walls.

5. The hand-held compact diagnostic device according to claim 4 wherein said rotation means includes a generally cylindrical housing member having opposed circular end faces each being perpendicular to said axis of rotation and each wall of said pair of opposite parallel side walls includes a raised annular boss for retaining a respective circular end face of a corresponding cylindrical housing member.

6. The hand-held compact diagnostic device according to claim 5 wherein each of said circular end faces includes a pair of diametrically opposed inwardly directed notches formed on the circumference of the circular face, at least one of each pair of said raised annular bosses has a circumferential opening, and each side wall having a respective boss with said circumferential opening, contains a flat spring tangential to the respective annular boss at a point including the opening, said flat spring having a pawl projecting through said circumferential opening into the area encircled by the respective annular boss whereby when a respective instrument head is rotated to the closed position, said pawl snaps into one of the notches to bias said instrument head closed, and when said instrument head is rotated to the fully extended position, said pawl snaps into the other notch to bias the head in the extended position.

7. The hand-held compact diagnostic device according to claim 5 wherein said adjustment means includes a collar having at least one bottom aperture and a threaded horizontal aperture with a set screw provided therein.

8. The hand-held compact diagnostic device according to claim 7 wherein said cylindrical housing member further includes a circular opening formed in the side thereof, said circular opening extending laterally between said opposed circular end faces and downwardly to an inwardly directed annular rim and said swivel means includes an adaptor comprising:

a generally cylindrical base member having an axis collinear with said central axis and an annular groove formed around an outer lower circumference thereof, said inwardly directed annular rim extending into said annular groove so that the base member turns relative to the housing member;

an outwardly directed circular flange segment centered around said central axis and formed on top of the base member; and a hollow shaft segment formed around the center of the flange segment and directed upwardly therefrom, the shaft segment having first means for receiving a lamp housing and lamp therein so that an insulated electrical terminal of the lamp extends into the interior of the base member and second means for securely receiving said respective instrument head thereabout so that the proximal end of the instrument head rests snugly against the flange segment.

9. The hand-held compact diagnostic device according to claim 8 wherein said second means for securely receiving said respective instrument head includes a single helical thread formed around an outer circumference of said hollow shaft segment, the single thread corresponding to a mating thread in the proximal end of said respective instrument head so that the proximal end of the instrument is quickly secured against the flange segment.

10. The hand-held compact diagnostic device according to claim 8 wherein said collar is positioned around said adaptor between the bottom of the flange segment and the upper edge of said annular groove so that it rests against said inwardly directed annular rim and said detent means includes at least one spring urged ball detent positioned below the rim, the ball protruding slightly thereabove through a slot therein so that the head may be adjusted into said aligned position while the collar is positioned with said bottom aperture directly above the protruding ball detent whereby when said set screw is tightened against the base member, the adaptor will be biased in said aligned position for enclosing the head within the containment area.

11. The hand-held compact diagnostic device according to claim 10 wherein said detent means includes two spring urged ball detents diametrically opposed across said annular rim and said collar includes four bottom apertures spaced at ninety degree intervals so that said respective instrument head is biased by two ball detents in said aligned position and in three additional potentially preferred positions for use along said predetermined arc length formed by said ninety degree intervals.

12. The hand-held compact diagnostic device according to claim 8 further including an electric switch means for activating said source of illumination when said respective instrument head is rotated into said fully extended position.

13. The hand-held compact diagnostic device according to claim 12 wherein said adaptor is made of an electrically conductive material, said cylindrical housing member is formed from a non-conductive material, and said switch means is positioned on one of the circular end faces of the housing and includes a first central electrical terminal that passes therethrough to contact said insulated electrical terminal of the lamp below said inwardly directed annular rim and a first radial electrical terminal, positioned adjacent the first central terminal on a radius extending therefrom, that passes through the face and contacts the bottom edge of the base member of the adaptor so that when said respective instrument head is turned, said first central and radial electrical terminals remain in contact with the lamp and base respectively.

14. The hand-held compact diagnostic device according to claim 13 wherein said switch means further includes a second central electrical terminal being in continuous contact with the first central terminal and a second radial electrical terminal positioned adjacent the second central terminal on a radius extending therefrom, the second terminals being connectable to a battery source containable in the case so that when said respective instrument head is rotated to the closed position, the radial terminals are disengaged thereby disconnecting a contained battery source from the lamp and when the head is rotated to the fully extended position, the radial terminals are in contact with each other thereby providing electric current from said contained battery source to the lamp.

15. The hand-held compact diagnostic device according to claim 14 wherein said battery source is accessed through second openable cover means.

16. The hand-held compact diagnostic device according to claim 2 including a pair of instrument heads and wherein said case is an elongated case having an axis of elongation and an opening at each end, said first cover means is parallel to said axis of elongation and extends from one open end to the other, and said axis of rotation is perpendicular to said axis of elongation.

17. The hand-held compact diagnostic device according to claim 16 wherein one of the pair of instrument heads is an ophthalmoscope and the other is an otoscope having a speculum portion, and said elongated case further includes a compartment for containing a plurality of replacement tips for said speculum portion of the otoscope and second openable cover means for enclosing said compartment.

* * * * *